(12) United States Patent
van den Dool et al.

(10) Patent No.: US 9,622,763 B2
(45) Date of Patent: Apr. 18, 2017

(54) INSTRUMENT FOR MINIMALLY INVASIVE SURGERY

(75) Inventors: Teunis Cornelis van den Dool, Delft (NL); Geerten Frans Ijsbrand Kramer, Utrecht (NL); Erik Tabak, Gouda (NL); Michiel Peter Oderwald, Delft (NL)

(73) Assignees: Nederlandse Organisatie voor toegepast-natuurwetenschappelijk onderzoek TNO, Delft (NL); Vleugels Holding B.V., Maastricht (NL)

( * ) Notice: Subject to any disclaimer, the term of this patent is extended or adjusted under 35 U.S.C. 154(b) by 1008 days.

(21) Appl. No.: 12/995,102

(22) PCT Filed: May 29, 2009

(86) PCT No.: PCT/NL2009/050299
§ 371 (c)(1),
(2), (4) Date: Feb. 16, 2011

(87) PCT Pub. No.: WO2009/145632
PCT Pub. Date: Dec. 3, 2009

(65) Prior Publication Data
US 2011/0137337 A1   Jun. 9, 2011

(30) Foreign Application Priority Data

May 30, 2008   (EP) .................................... 08157291

(51) Int. Cl.
*A61B 17/00* (2006.01)
*A61B 17/29* (2006.01)
*A61B 90/00* (2016.01)

(52) U.S. Cl.
CPC ........ *A61B 17/29* (2013.01); *A61B 2017/294* (2013.01); *A61B 2017/2939* (2013.01); *A61B 2090/065* (2016.02)

(58) Field of Classification Search
CPC ........ A61B 17/2804; A61B 2017/2938; A61B 17/29–17/2955; A61F 19/465
(Continued)

(56) References Cited

U.S. PATENT DOCUMENTS 5,078,466 A    1/1992  MacCulloch
5,269,804 A *  12/1993 Bales et al. .................... 606/205
(Continued)

FOREIGN PATENT DOCUMENTS

DE    93 20 348 U1    5/1994
DE    10127506 A1     1/2003
(Continued)

*Primary Examiner* — Elizabeth Houston
*Assistant Examiner* — Lindsey Bachman
(74) *Attorney, Agent, or Firm* — Kilpatrick Townsend & Stockton LLP (57) ABSTRACT

The invention relates to an instrument, preferably for minimally invasive surgery, comprising a frame (27) having a proximal end and a distal end, a first working element (4) having a first origin located at the distal end and a second working element (5) having a second origin and being arranged at the distal end cooperating with the first working element, a force sensor for measuring a force exerted on at least one of the said first and the second working elements, wherein the distal end of the frame comprises an opening (23) between the first origin and the second origin, the force sensor being arranged on the frame in a vicinity of the opening.

19 Claims, 11 Drawing Sheets

(58) Field of Classification Search
USPC .................. 606/205, 50–52; 600/562, 564; 73/856–860
See application file for complete search history.

(56) References Cited

U.S. PATENT DOCUMENTS

| | | | |
|---|---|---|---|
| 5,413,492 A | | 5/1995 | Obata |
| 5,689,606 A | | 11/1997 | Hassan |
| 5,720,742 A | | 2/1998 | Zacharias |
| 6,024,514 A | | 2/2000 | Ostergaard |
| 6,146,394 A | | 11/2000 | Morejohn et al. |
| 6,389,193 B1 | | 5/2002 | Kimmel et al. |
| 6,582,451 B1 | | 6/2003 | Marucci et al. |
| 6,616,667 B1 | | 9/2003 | Steiger et al. |
| 6,928,947 B1 | | 8/2005 | Clapham |
| 6,934,457 B2 | | 8/2005 | Vincent et al. |
| 7,155,316 B2 | | 12/2006 | Sutherland et al. |
| 7,169,167 B2 | * | 1/2007 | Chu ............................. 606/205 |
| 7,210,556 B2 | | 5/2007 | Bath et al |
| 7,211,099 B2 | | 5/2007 | Lang et al |
| 2002/0188316 A1 | | 12/2002 | Dingler |
| 2004/0225323 A1 | * | 11/2004 | Nagase et al. ............... 606/205 |
| 2006/0159524 A1 | | 7/2006 | Thompson et al. |
| 2006/0200049 A1 | * | 9/2006 | Leo et al. ..................... 600/587 |
| 2007/0036506 A1 | | 2/2007 | Kewitsch |
| 2007/0074584 A1 | | 4/2007 | Talarico et al. |
| 2007/0078484 A1 | * | 4/2007 | Talarico et al. ............... 606/205 |
| 2007/0151391 A1 | | 7/2007 | Larkin et al. |
| 2007/0156019 A1 | | 7/2007 | Larkin et al. |
| 2008/0065098 A1 | * | 3/2008 | Larkin .......................... 606/130 |
| 2008/0065111 A1 | * | 3/2008 | Blumenkranz et al. ...... 606/130 |
| 2011/0046637 A1 | * | 2/2011 | Patel ..................... A61B 17/29 606/130 |

FOREIGN PATENT DOCUMENTS

| | | |
|---|---|---|
| EP | 1429163 A2 | 6/2004 |
| EP | 1660852 A1 | 5/2006 |
| WO | 03/005062 A1 | 1/2003 |
| WO | 03/020139 A2 | 3/2003 |
| WO | WO 03/020139 A2 | 3/2003 |
| WO | 03/056132 A1 | 7/2003 |
| WO | 2006/010326 A1 | 2/2006 |
| WO | 2007/044684 A2 | 4/2007 |
| WO | WO 2007/111737 A2 | 10/2007 |
| WO | WO 2009/009220 A2 | 1/2009 |

* cited by examiner

INSTRUMENT FOR MINIMALLY INVASIVE SURGERY

CROSS-REFERENCES TO RELATED APPLICATIONS

This application is a National Stage of International Application No. PCT/NL2009/050299, filed May 29, 2009, and which claims the benefit of European Patent Application No. 08157291.9, filed May 30, 2008, the disclosures of which are incorporated herein by reference.

FIELD OF THE INVENTION

The invention relates to an instrument comprising:
a frame having a proximal end and a distal end;
a first working element having a first origin located at the distal end;
a second working element having a second origin and being arranged at the distal end cooperating with the first working element;
a force sensor for measuring a force exerted on at least one of the said the first and the second working elements.

BACKGROUND OF THE INVENTION

An instrument as is set forth in the opening paragraph is in particular suitable for minimally invasive surgery, in course of which, usually, an elongated mechanism having substantially small cross-section is introduced via an incision into a body of a patient. The mechanism may comprise a handle or any other suitable actuator or mechanism for operating the first and the second working elements, for example, miniature forceps, miniature scissors, or the like. It is of paramount importance to first, apply sufficient force to the first and the second working element on one hand, and to provide accurate feedback of the applied force to the operator.

An embodiment of an instrument for minimally invasive surgery is known from WO 03/020139. In the known instrument the external force exerted on the forceps by a surgeon is being measured by a force sensor arranged on a jaw of the forceps and is feed-back to the surgeon via a control unit. In this way the surgeon can have a feeling of the applied force. The force sensor may be connected by means of a glass fiber to a suitable control unit.

It is a disadvantage of the known instrument in that an accuracy of the force measurement is affected by external factors, like ambient temperature and signal loss caused by undesirable deflection of the fiber due to the fact that it runs over a hinge of the working element. It is a further disadvantage of the known instrument that the gripping force measurement by the force sensor on the forceps is dependent on the axial position of the tissue in the forceps.

Another embodiment of a surgical instrument is known from U.S. Pat. No. 6,616,667. It is a disadvantage of the known surgical instrument that force sensor signals are routed along hinges, which decreases accuracy of the measurement.

A still another embodiment of a surgical instrument is known from WO2007/111737. It is a disadvantage of the known surgical instrument that, by way of its construction and sensor arrangement, it cannot measure gripping force independently of a position of tissue in the jaws.

SUMMARY OF THE INVENTION

It is an object of the invention to provide an instrument, in particular for minimally invasive surgery, wherein the force exerted on the first and/or second working element is determined with higher degree of accuracy.

To this end in the instrument according to the invention the distal end of the frame comprises an opening between the first origin and the second origin, the force sensor being arranged on the frame in a vicinity of the opening.

The technical measure of the invention is based on the insight that by provision of the force sensor on the frame any signal distortion due to the movement of the first and/or the second working element is avoided. Additionally, the measured force can be made independent of the position of the tissue in the working elements. It is found that by provision of an opening between the first origin and the second origin a force measurement with increased sensitivity is enabled. The opening may be realized by a slit, or by means of one or more bore holes arranged in the area between the first origin and the second origin.

In an embodiment of the instrument according to the invention the first working element is pivotable about a first hinge and/or the second working element is pivotable about a second hinge.

It is found, by virtue of Newton's third law that the forces applied by the first and the second working elements in use to the surrounding, for example to a tissue, manifest themselves as reaction forces to the hinge where about these elements pivot. Therefore, by providing the first and/or the second working elements with a dedicated hinge, the accuracy of the force measurement is improved, in particular because the measured force can be made independent of the position of the tissue in the working element and due to the fact that both force components are measured independently from each other. In addition no vulnerable sensor signals need to be transferred over the rotating hinges, which could cause damage to the sensor wires or fibres.

Preferably, for the force sensor one or more strain sensors are used. Strain sensors can be used to measure force because a force increment dF causes a strain dx as described by Hooke's law: $F=E \cdot dx$, where k is the modulus of elasticity. Also strain can be used to measure temperature because temperature increment dT causes a material to extend: $dx=a \cdot dT$, where a is the coefficient of thermal expansion.

In a still further embodiment of the instrument according to the invention a plurality of strain sensors is provided, wherein at least one strain sensor is arranged for measuring a linear sum of several effects such as gripping force, rod pulling force, and vertical force resulting from the rod force, which results in apparent gripping force. The strain sensors may be arranged in the vicinity of the opening to optimize the sensitivity for gripping forces on the tissue.

At least one strain sensor is preferably provided in order to avoid signal misinterpretation due to ambient influences, for example temperature or interfering forces. For example, it is possible that a pair of strain sensors is provided wherein a first strain sensor is used for determining the force exerted by a forceps jaw, wherein the second strain sensor is used as reference for compensating for strain and pressure forces along the frame. Such forces can occur due to pushing or pulling forces on the rod, but can also occur due to manipulation of tissue with the jaws other than gripping. Such an arrangement with extra sensors and how to derive gripping force from them is explained in conjunction with the detailed description of FIG. 10.

In addition, it is found that friction in an axis where about a working element is pivotable may cause undesired distortion to the measured signal. By using a suitable plurality of the sensors for measuring a force exerted by a working element force measurement with increased accuracy is enabled by combination of data measured at the plurality of measurement points. In practice this might be implemented by the calibration method elaborated in conjunction with FIG. 10 and performing a calibration for closing and opening direction separately.

Preferably, a suitable plurality of strain sensors is integrated on a mutual optical fiber. The fiber may be arranged in a suitable cavity provided in the frame or on a surface of the frame. It will be appreciated that in case when both the first working element and the second working element are pivotable respective pluralities of strain sensors are provided. In this case two optical fibers may be envisaged. More preferably, each optical fiber may be provided in a high-frequency shielded environment for protecting tissue from potentially hazardous influence of high frequency signals transmitted through these fibres.

A single extra sensor cannot be used to compensate for 2 effects. At least 1 extra sensor is needed to compensate for spurious forces and at least 1 other additional sensor is needed to compensate for temperature. Such a temperature reference is preferably put on a part of the frame that doesn't carry mechanical stress. Extra sensors will be explained in more detail with reference to FIG. 11.

In a further embodiment of the instrument according to the invention at least one of the working elements comprises a strain sensor arranged for measuring a temperature of the distal end of the instrument.

It is found to be particularly advantageous to build-in a temperature sensor in the distal portion of the instrument. Such measurement may be advantageous during interventions, when it is preferable to measure local tissue temperature prior to any handling. For example, in some cases it might be necessary to determine absence of inflammation, which is characterized by an increase of the local temperature.

In accordance with this feature, force measurements can be carried out independently of the tissue temperature, by means of application of suitable correction factors and/or sensor temperature calibration data. In particular, local deformations of the working elements and/or frame due to temperature differences may be accounted for. As a result a temperature invariant force measurement is enabled. Additionally or alternatively, for example, during coagulation procedure, the distal portion of the instrument can be used to measure temperature of the tissue independently, which is advantageous for preventing excessive tissue damage due to overheating.

In a further embodiment of the instrument according to the invention, the instrument comprises a control unit arranged to determine a feedback signal conceived to be used for controlling the first working element and/or the second working element.

This feature has an advantage that accuracy of the manipulation of the working elements arranged at the distal portion of the apparatus can be substantially increased due to the fact that, first, the respective forces applied by the working elements to the tissue are measured with increased accuracy and, secondly, due to the fact that the relative displacement and mutual position of the working elements is controlled based on the feed-back signal provided by the control unit on basis of suitable analysis of said measured forces. This feature will be explained in more detail with reference to FIGS. 7-9.

In a particular embodiment of the instrument according to the invention the one or more strain sensors are implemented as Fibre Bragg Grating (FBG) sensors.

It is found to be advantageous to use FBG sensors. An example of the FBG sensor is described in WO01/84097 A1 and will not be explained here in detail. An application of the FBG sensors as strain gauges is advantageous because a wavelength shift is proportional to a degree of strain, which is independent of any loss in the signal intensity thereby improving accuracy of force measurement. Furthermore an FBG doe not comprise any electrical signals near the sensitive measurement area. This is especially important in minimally invasive surgery instruments, which tend to include high voltage and high frequency electrical signals for surgical purposes, such as cutting.

Preferably, a plurality of FBG sensors is integrated on a mutual optical fiber. According to this feature a total number of constructive elements of the instrument is decreased due to the fact that respective signals generated by a suitable plurality of the FBG sensors propagate over a mutual optical fiber. Preferably, the frame of the instrument comprises a cavity and the optical fiber is arranged in said cavity.

These and other aspects of the invention will be discussed in further detail with reference to drawings, wherein like reference signs relate to like elements. It will be appreciated that the drawings are presented for illustrative purposes and may not be used to limit the scope of protection of appended claims.

DETAILED DESCRIPTION OF THE DRAWINGS

Figure 1:
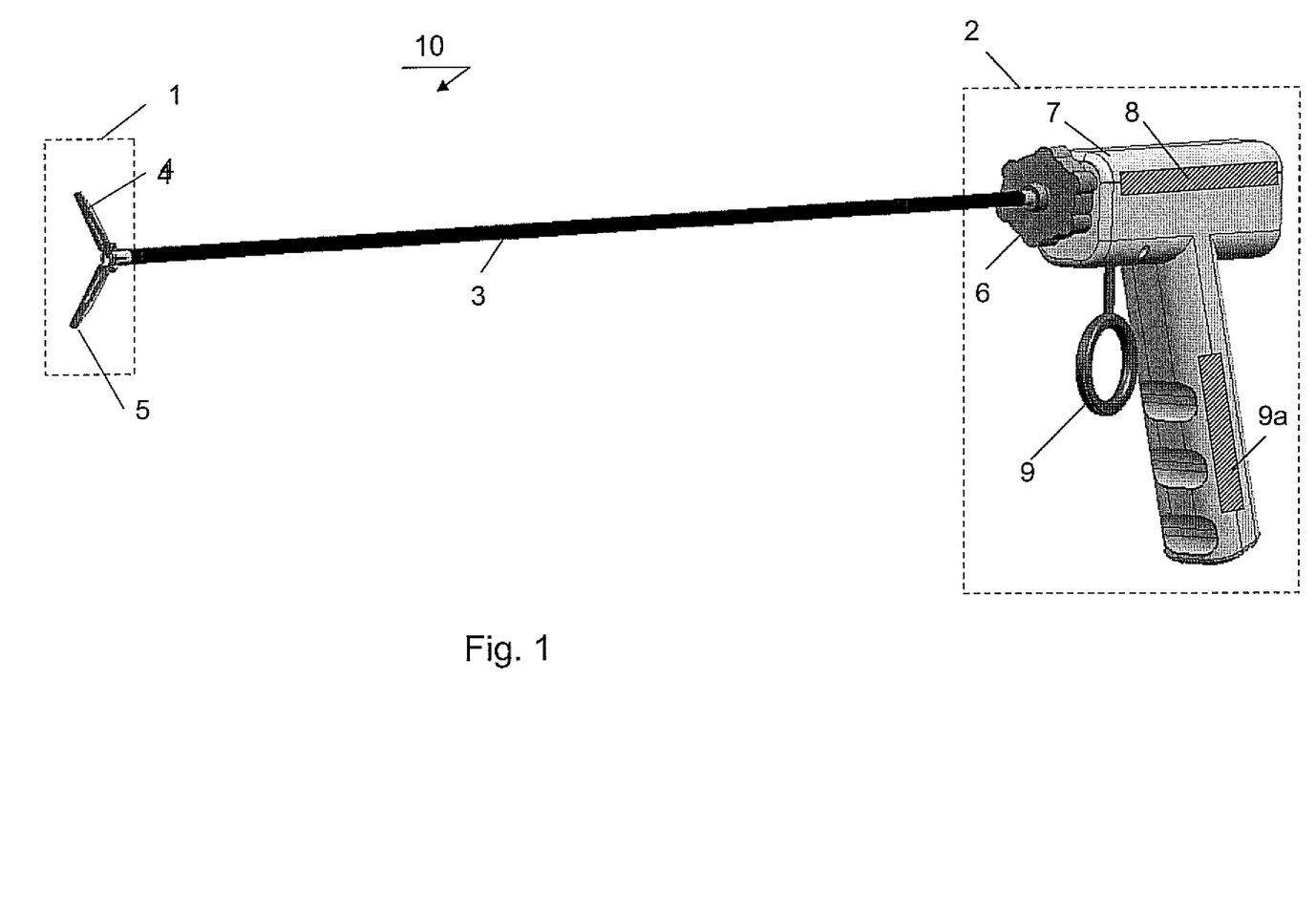
FIG. 1 presents a schematic view of an embodiment of a device according to the invention.

FIG. 1 presents a schematic view of an embodiment of a device according to the invention. The device 10 may be applicable in the field of surgery, in particular in the field of minimally invasive surgery. The device 10 comprises a proximal end 2 having a control handle 7 provided with a trigger ring 9 conceived to operate a first working element 4 and/or a second working element 5 arranged at a distal portion 1 of the device 10. It will be appreciated that the working elements 4, 5 may be suitable for pinching, clamping, gripping, stapling, holding a further instrument, cutting, squeezing, or the like. In order to operate the working elements 4, 5 the handle 7 may comprise a motor 8 arranged for inducing a suitable displacement of the working elements 4, 5 with respect to the frame 3. The handle may further comprise a motor 9*a* for motorizing the trigger 9. The frame 3 may be arranged as a hollow body wherein an actuation rod (not shown) for actuating the working elements 4, 5 is provided. In addition, the frame 3 may comprise suitable fibers connecting to the force sensors arranged on the frame 3 in a vicinity of origins of the working elements 4, 5. It will be appreciated that the term 'origin' may relate to a pivot point of the working element, or, otherwise, may relate to a region where the frame mouths into a stationary working element. The handle 7 may further comprise a shaft rotator 6 arranged for connecting the frame 3 and its components, like the fibers and the actuation rod to the motor 8 and a detector (not shown).

Figure 2:
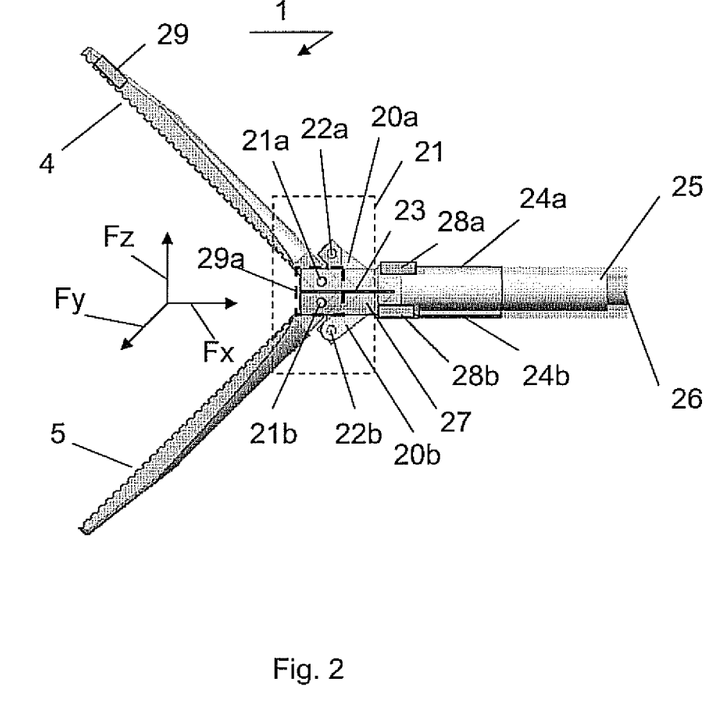
FIG. 2 presents a schematic view of a close-up of a distal portion of the device of FIG. 1.

FIG. 2 presents a schematic view of a close-up of a distal portion of the device of FIG. 1. The distal portion 1 of the device according to the invention may comprise a forceps having a first jaw 4 and a second jaw 5. In accordance with the invention an opening 23 is provided in the frame 27 in a region near the origin 29*a* of the first jaw 4 and the second jaw 5. The opening may be in a form of a slit. The forces exerted by the jaws 4, 5 to a tissue in use are measured by the force sensors 28*a*, 28*b*. The signal from the sensors 28*a*, 28*b* may be transported to a suitable detector (not shown) by means of respective optical fibers 24*a*, 24*b*. Due to use of an optical transmission a substantially interference-free signal line is provided. The fibers 24*a*, 24*b* preferably run in respective fiber channels provided on a surface of the frame 27.

In accordance to a further aspect of the invention both the first jaw 4 and the second jaw 5 are arranged with dedicated individual hinges 21*a*, 22*a*. Due to this the reaction forces applied to a suitable jaw displacement mechanism 21 are measured independently of the position of tissue in the jaws 4 and 5 thereby increasing accuracy of force measurement. Also the sensors 28*a* and 28*b* are on the frame 27 and not on any of the moving parts of the distal portion of the device such that vulnerable sensor wiring doesn't have to cross hinges.

The jaw displacement mechanism 21 may be arranged with a suitable plurality of further pivots for enabling an envisaged displacement trajectory of the jaw tips. The mechanism 21 may comprise a doubly segmented bar 20*a* and 20*b*, which may be operable by the actuation rod 26 connected to a suitable fitting, for example a bayonet fitting 25.

In accordance with the present embodiment it is possible to measure grip forces of the jaws 4, 5 as well as tangential, radial and axial forces. Measurement of axial Fx and vertical Fz forces as well as tangential momentum My can be easily measured using the depicted apparatus. It will further be appreciated that further forces could be measured by supplementing the arrangement as shown in FIG. 2 with one or more sensors in a transverse direction with respect to the frame 27. It will further be appreciated that the arrangement of FIG. 2 may be configured to enable measurement of forces and moments in different directions (Fx, Fy, Fz, Mx, My, Mz) as well as a total grip force exerted by the first and second working elements. It will be appreciated that suitable arrangement of a plurality of sensors for enabling due measurement of forces, moments and torque lies within ordinary skill of the artisan.

In addition, it is possible to provide a supplementary temperature sensor 29 at a tip of one or both working elements. This has an advantage of enabling a direct tissue measurement using working elements 4, 5 post application of coagulation or electrosurgery. In this case the working elements 4, 5 may indicate whether the tissue or the working elements have appropriately cooled down. Preferably, the temperature sensor comprises an FBG sensor.

Figure 3:
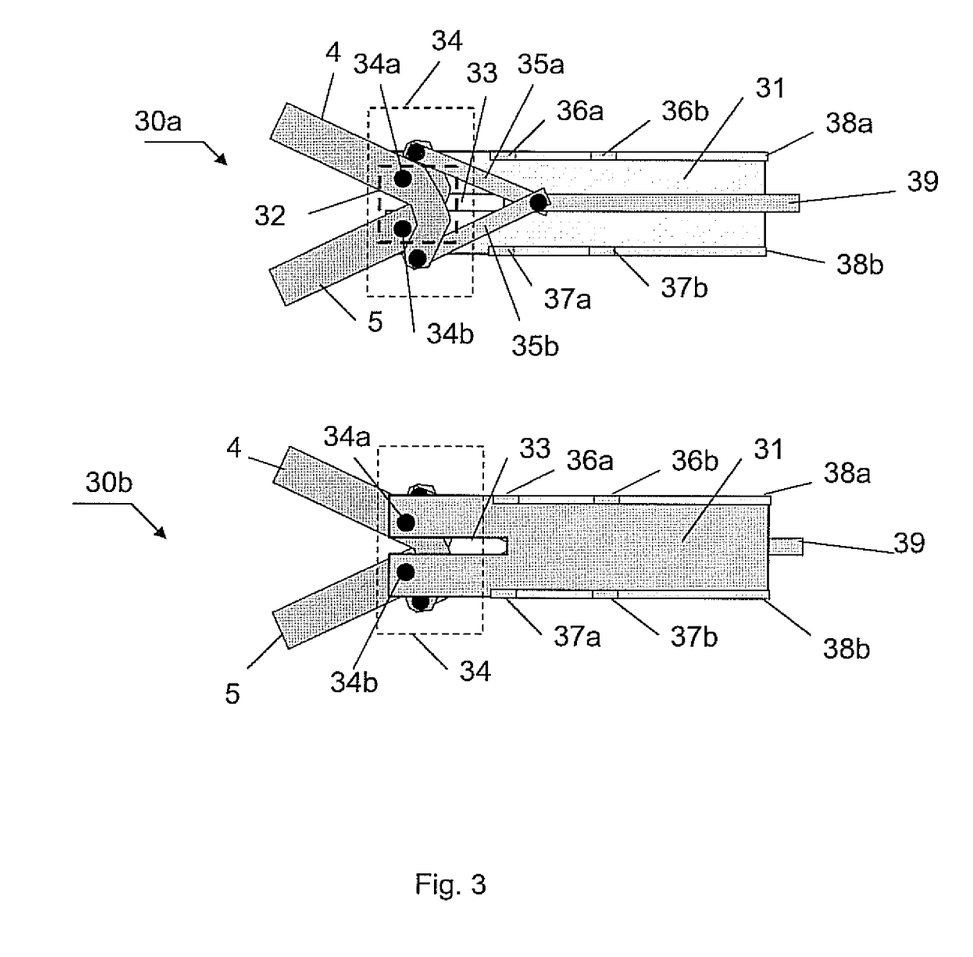
FIG. 3 presents a schematic view of an embodiment of a forceps mechanism of the device of FIG. 2.

FIG. 3 presents a schematic view of an embodiment of a forceps mechanism of the device of FIG. 2, schematically depicting a left and a right view with respect to an imaginary cut centerline. Detail 30*a* shows forceps jaws 4, 5 being displaceable using a mechanism 34 comprising a suitable plurality of mechanically connected segments, whereby each jaw is pivotable about its own pivot 34*a*, 34*b*. The mechanism is controllable by the actuation rod 39. In accordance to the invention, in the area nearby the origin of the jaws 32 a slit-shaped opening 33 is provided in the frame 31. The forces are measured by the force sensors 36*a*, 36*b* and 37*a*, 37*b*. Each pair of force sensors is connected to a dedicated fiber 38*a*, 38*b*. Preferably, one sensor from the pair is used as a reference sensor in order to compensate for possible signal deviation due to ambient temperature and/or tangential and/or axial forces. Preferably, the fibers 38*a*, 38*b* are covered by a high-frequency shield, which may be arranged as a suitable sleeve on the frame 31. Such a shield may be required for instruments that are also used for transferring a high frequency signal and/or a high voltage energy to the jaws, for example for cutting tissue.

Detail 30*b* depicts a left view of the forceps 4, 5, whereby the opening 33 is better visible. It will be appreciated that the sensors 36*a*, 36*b*, 37*a*, 37*b* may be arranged in a suitable vicinity of the opening 33, it is not necessary to position them exactly above or below the opening for reaching the same effect of improving accuracy of force measurement.

It will be appreciated that FIG. 3 gives an example of an arrangement in which sensors 36*a* and 37*a* have maximum sensitivity for gripping force through bending moments in the two origins, whereas (reference) sensors 36*b* and 37*b* have maximum sensitivity for other forces such as pushing and pulling forces in the rod 39.

Figure 4:
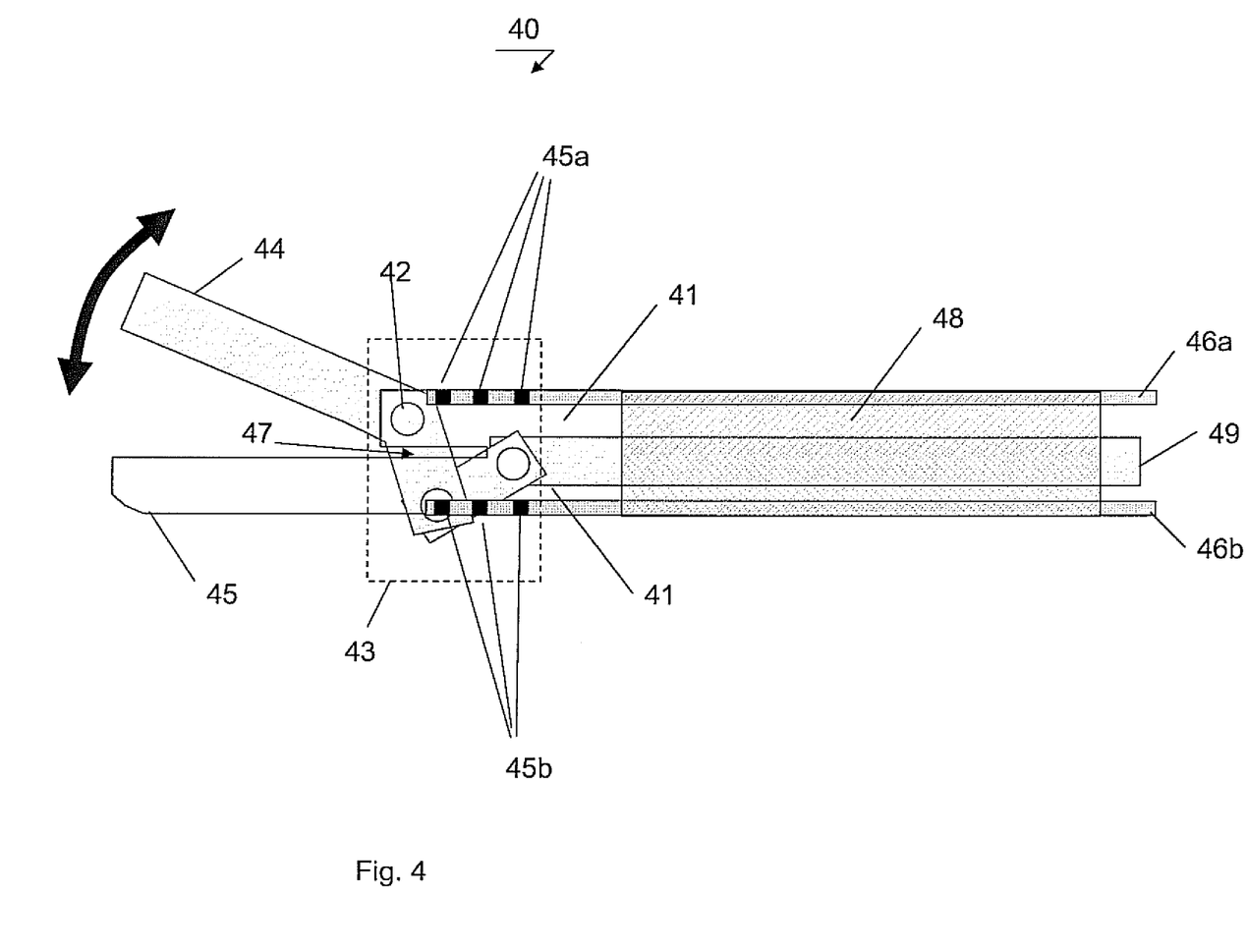
FIG. 4 presents a schematic view of a further embodiment of the device according to the invention.

FIG. 4 presents a schematic view of a further embodiment of the device according to the invention. In this embodiment the device 40 comprises a stationary jaw 45 and a movable jaw 44, which is displaceable about a pivot 42 by means of a mechanism controlled by the actuation rod 49, connected to the handle discussed with reference to FIG. 1. In accordance with the invention an opening 47 is provided in the frame 41 in a region 43 of the respective origins of the jaws 44, 45. Also in this embodiment the forces exerted by the jaws 44, 45 are measured by the force sensors 45*a*, 45*b* and the corresponding signals are transported by respective fibers 46*a*, 46*b*. It will be appreciated that although in this Figure three sensors 45*a* and three sensors 45*b* are indicated, any suitable plurality of sensors may be used depending on required accuracy of the force measurement. The frame 41 may further comprise electrical shield 48, which is arranged to protect tissue outside the frame 41 from high voltage and/or high frequency electric signals propagating through the frame, which signals may be used, for example for cutting or coagulating tissue with the jaws 44 and 45.

It will be appreciated that embodiment shown in FIG. 4 can also be adapted to comprise sensors along the lower jaw only. For example, a plurality of sensors along the lower (fixed) jaw 45*b* may be used for detecting at which position the tissue is inside the jaw and what force is exerted on the tissue.

Figure 5:
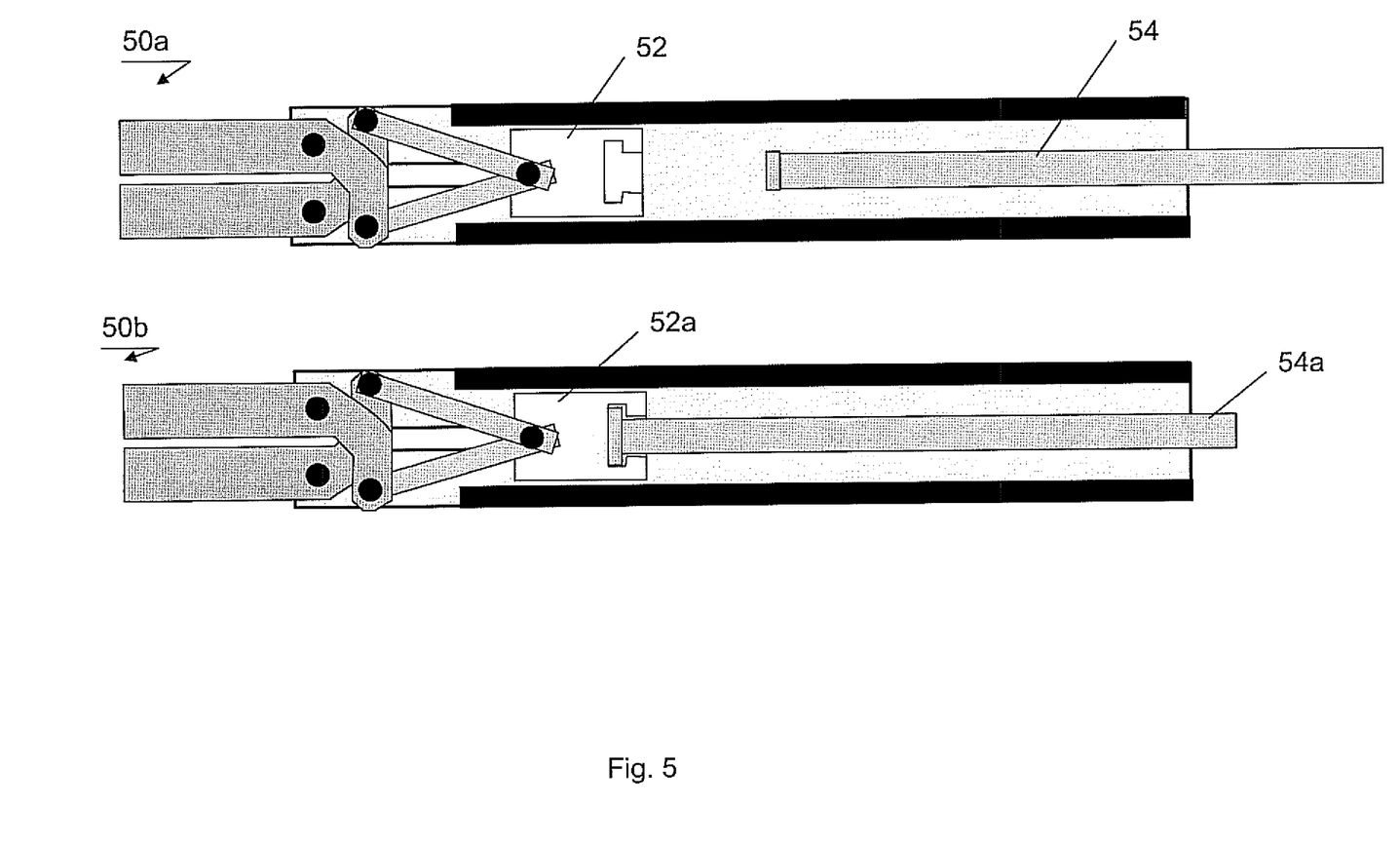
FIG. 5 presents a schematic view of the device according to the invention, provided with a removable distal portion.

FIG. 5 presents a schematic view of the device according to the invention, provided with a removable distal portion. Detail 50*a* schematically depicts the distal portion of the device as discussed with reference to FIG. 1, wherein the actuation rod 54 is disconnected from a locking mechanism 52. It will be appreciated that a great plurality of possible locking mechanisms 52 cooperating with the rod 54 are possible. When the distal portion has to be cleaned or replaced the rod 54a may be disengaged with the locking mechanism 52a, as depicted in detail 50a.

Figure 6:
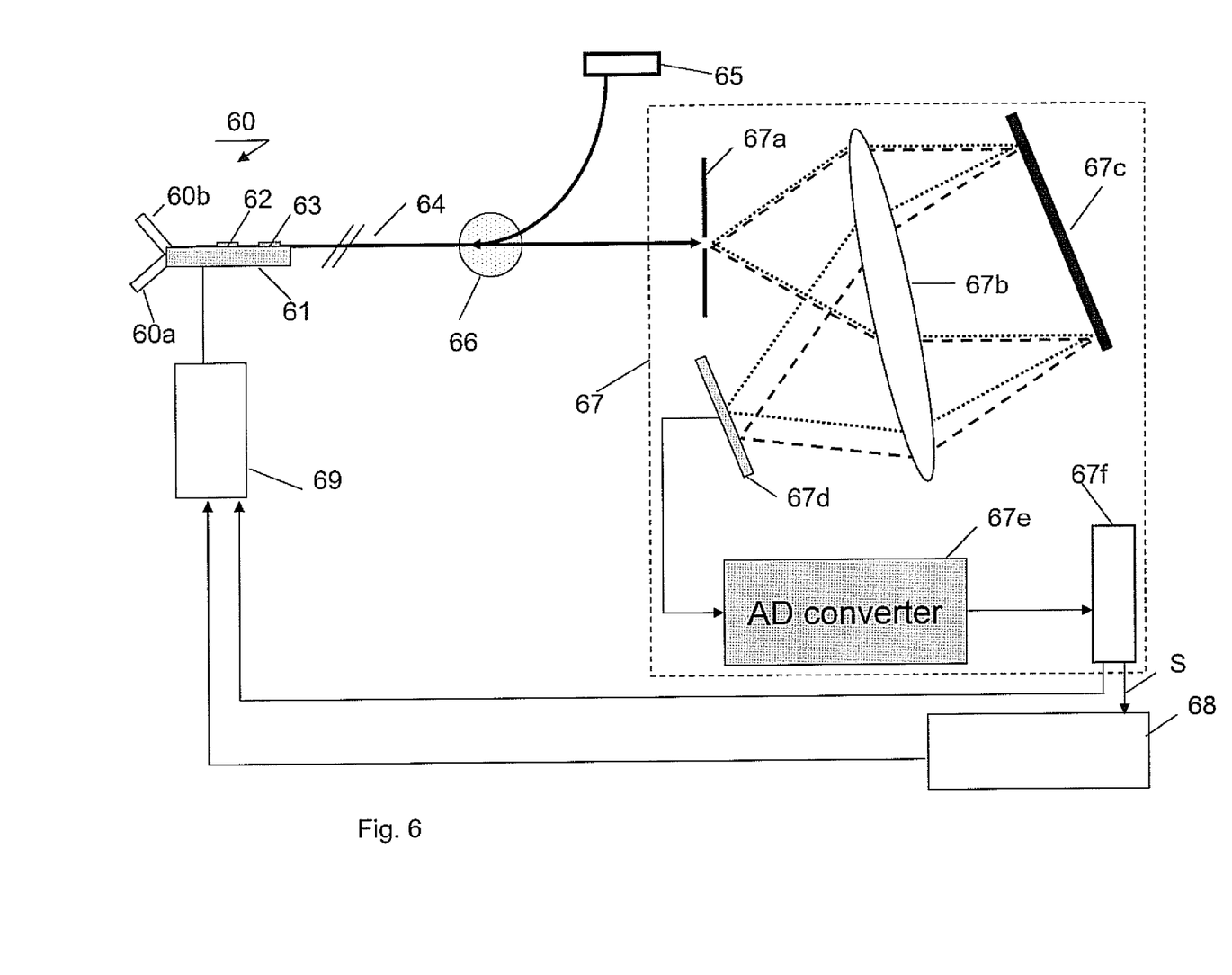
FIG. 6 presents a schematic view an embodiment of a device according to the invention provided with FBG sensors.

FIG. 6 presents a schematic view an embodiment of a device according to the invention provided with FBG sensors. In accordance with a further aspect of the invention the sensors 62, 63 arranged on the frame 61 of the device as is discussed with a reference to the foregoing are arranged to operate as an optical wavelength analyzer, for example as described in WO 01/84097. For this reason the device 60 may further comprise a light source 65, preferably arranged to generate a radiation beam in a broad band range, for example having wave length in a range of λ=1525-1560 nm. The light beam from the source may be introduced into the fiber 64 at location 66, which may be implemented as any suitable light connector. The force sensors, implemented as FBG are preferably arranged to reflect a specific wavelength, whereby strain in the FBG's will cause a shift of the reflected wavelength, the shift being representative to the amount of strain. The radiation beam having one or more shifted wavelengths will impinge on the optical wavelength analyzer 67 comprising a slit 67a, a suitable series of optical elements 67b, 67c, a detector 67d, an ADC converter 67e and a suitable processing means 67f.

The detector 67d may comprise a suitable plurality of detector elements and may be arranged to determine a wavelength shift of the impinging radiation beam, for example using an a-prior established correlation between a detector element having a specific position and a wavelength expected at that position. The optical elements may comprise lenses, mirrors, gratings, prisms, or any combination thereof. As a result an accurate system for determining an absolute value of the force exerted by one or more working elements is provided, improving overall reliability of the device.

Preferably, the processing means 67f is arranged to provide a feedback signal conceived to be used for controlling the working elements 60a, 60b. It will be appreciated that the control signal S is related to an absolute value of the force conceived to be applied by the working elements 60a, 60b to the tissue alone or in combination. The control signal S may be supplied to a suitable robot 68 conceived to operate the motor 69 arranged in the proximal end of the instrument 60. Alternatively, the control signal S may be directly applied to the motor 69 arranged in the proximal end of the instrument, as is discussed with reference to FIG. 1. Still alternatively, the control signal may be provided to a further actuator conceived to control the first working element and/or the second working element, for example the trigger 9 discussed with reference to FIG. 1. According to this feedback feature reliability of operation of the instrument according to the invention is further increased.

Figure 7:
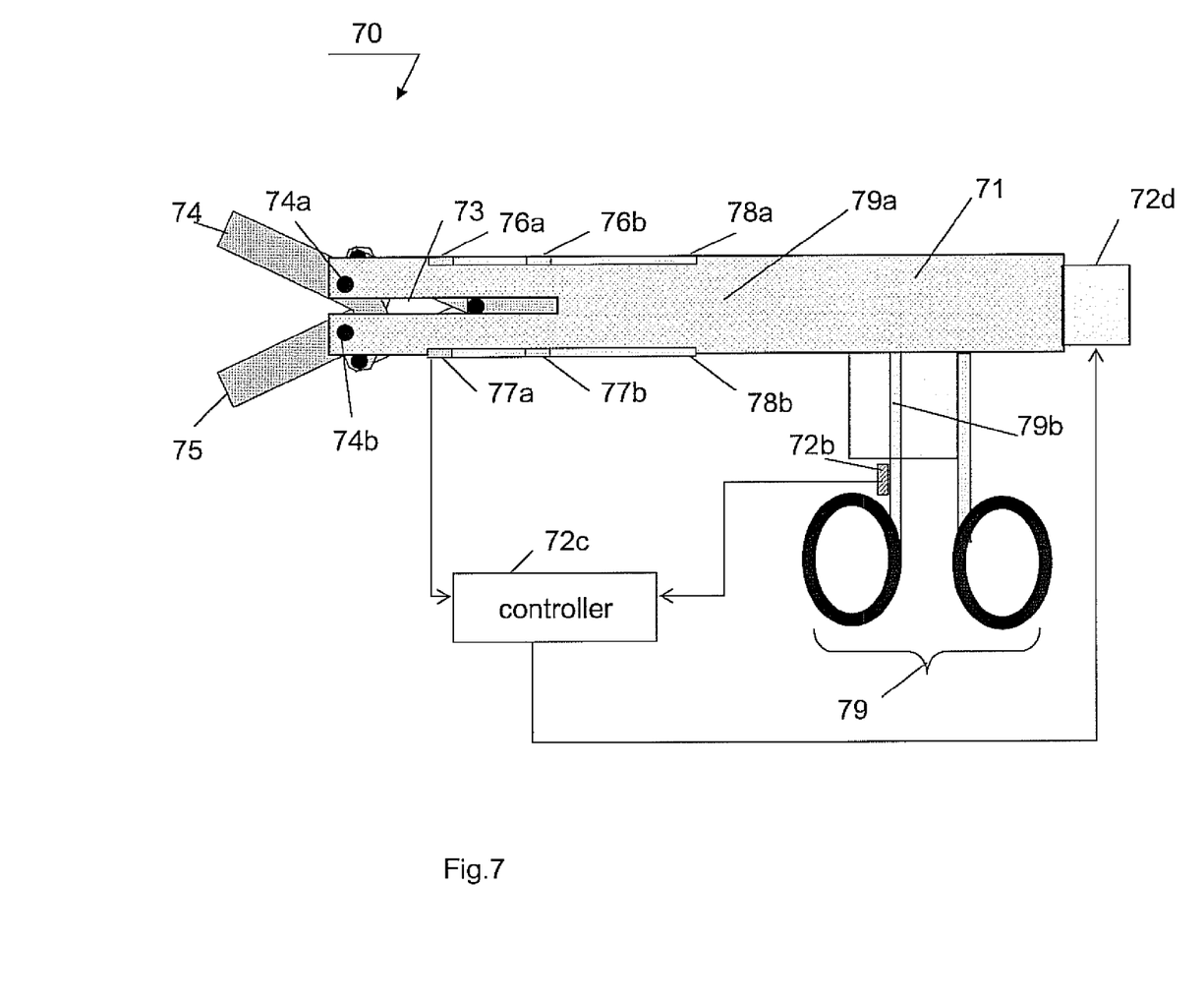
FIG. 7 presents a schematic view of an embodiment of a device according to the invention provided with feed-back functionality.

FIG. 7 presents a schematic view of an embodiment of a device according to the invention provided with feed-back functionality. Although FIG. 7 elaborates on an embodiment schematically shown in FIG. 3, it will be appreciated that the principles discussed herewith may be applied not only to the device according to the invention, but also to the device as known from the prior art.

Device according to the invention comprises a frame 71 arranged with a first working elements 74 and a second working element 75, which may be pivotably arranged with respect to the axes 74a, 74b. It will be appreciated that it is also possible that only one of the working elements is pivotably arranged. An opening 73 is provided in a vicinity of respective origins of the first working element and the second working element. In order to measure forces exerted by the first working element and the second working elements the frame 71 may be provided with sensors 76a, 76b, 77a, 77b which may be arranged on respective mutual fiber 78a, 78b. The fibers are preferably provided in a cavity running along the frame 71. Alternatively, the sensors may be arranged on the working elements 74, 75. The first working element and the second working element 74, 75 are controllable by means of a trigger 79, which may be manually operated. The trigger 79 is connected by means of suitable rods 79a, 79b to either or both the first working element 74 and the second working element 75 for enabling suitable displacement thereof. The trigger may be provided with a sensor 72b for measuring a force exerted on the trigger 79.

In accordance with the current embodiment the device 70 comprises a control unit 72c whereto signals from the sensors 72b, 76a, 76b, 77a, 77b are fed. Based on these signals the control unit is arranged to generate a feed-back signal for controlling the actuator 72d of the trigger unit 79 for suitably displacing the first working element 74 and the second working element 75. The actuator 72d may relate to a motor discussed with reference to FIG. 1 for enabling mechanical connection to the first and/or the second working elements. As a result the apparatus 70 according to the invention comprises a self-contained system for operating the first and/or the second working element in response to an initial handling of an operator.

Figure 8:
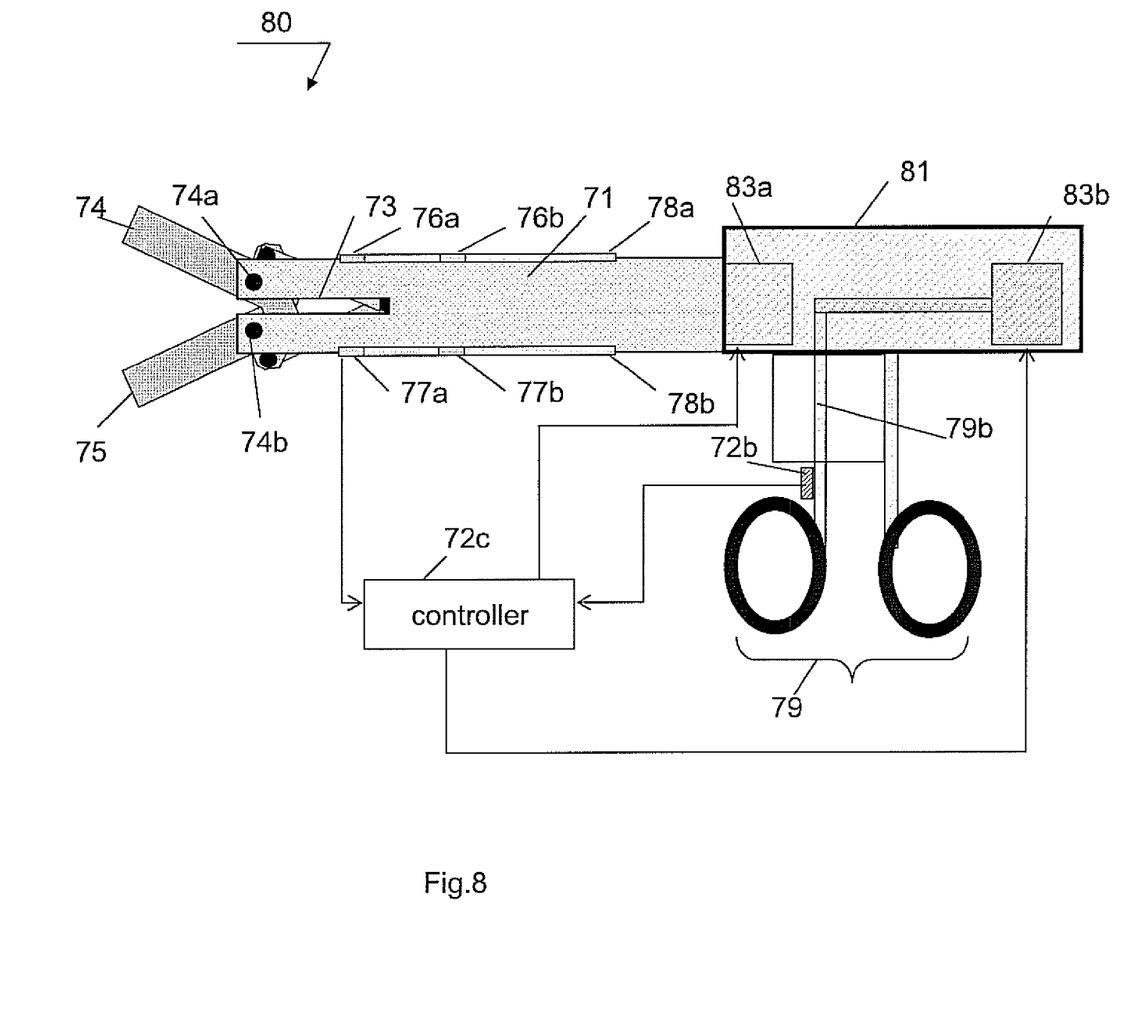
FIG. 8 presents a schematic view of a further embodiment of the device as shown in FIG. 7.

FIG. 8 presents a schematic view of a further embodiment of the device as shown in FIG. 7. In this embodiment the device 80 comprises a control box 81 arranged to enable wired gripping. In this embodiment, the control unit 72c is arranged to provide the feed-back signal to the actuator 83b, which may be arranged in electronic connection with a further actuator 83a arranged to displace the first working element 74 and/or the second working element 75. It will be appreciated that the electronic connection is not limited to suitable wiring, but may comprise a micro-processor arranged to determine a control signal to the actuator 83a in dependence of a signal fed into it by the sensors 78 and 72b and control unit 72c.

In addition, the actuator 83b, may be arranged to feed-back the force exerted by the first working element and the second working element to suitable handles of the trigger 79 so that the operator is provided with accurate indication on the exerted force.

Figure 9:
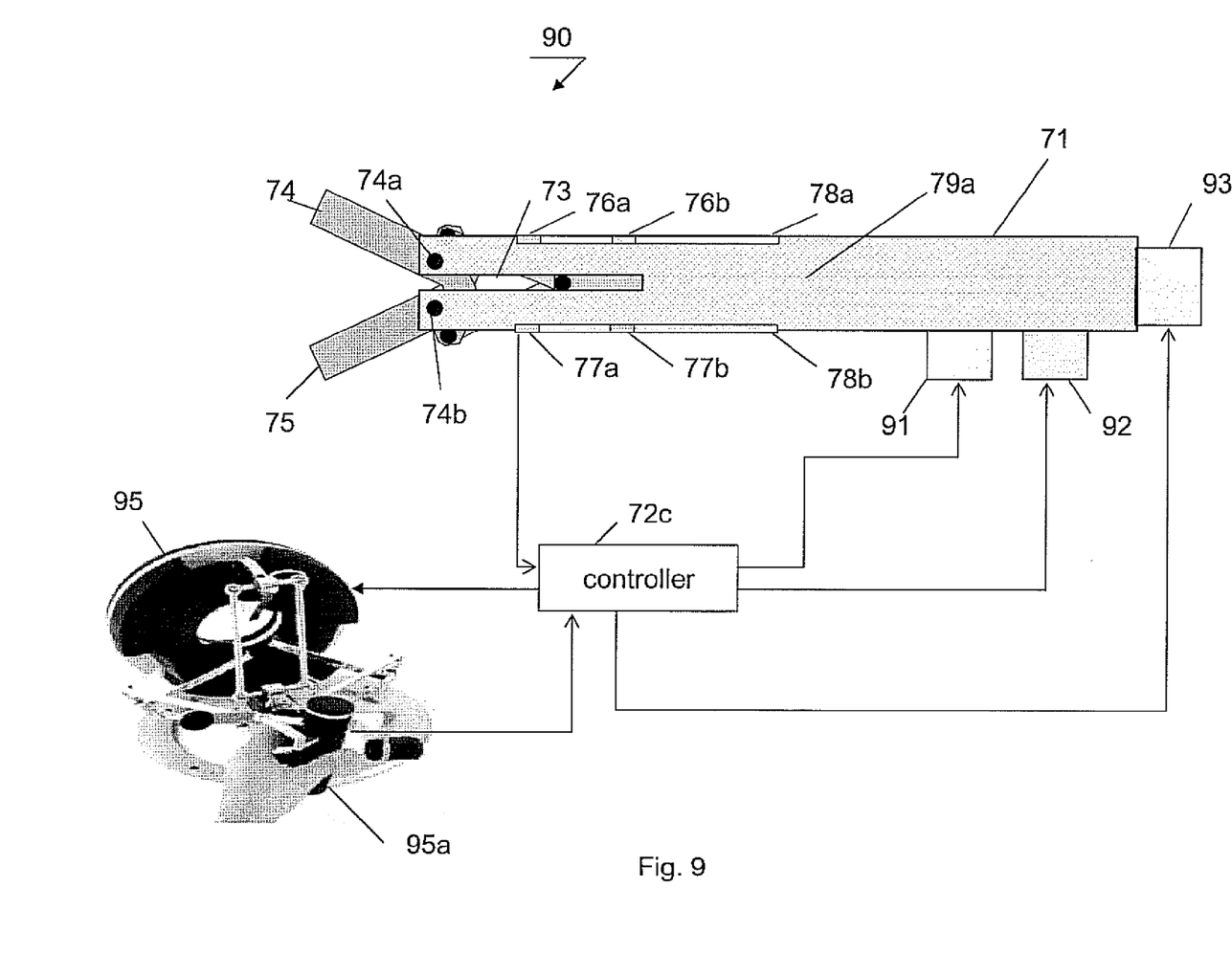
FIG. 9 presents a schematic view of an embodiment of the device as shown in FIG. 8.

FIG. 9 presents a schematic view of an embodiment of the device as shown in FIG. 8. In this particular embodiment, the device 90 is provided with a robotic unit 95 conceived to operate the first working element 74 and/or the second working element 75 by means of suitable actuators. The device 90 is arranged with the control unit 72c for receiving data from the robotic unit and from the sensors 76a, 76b, 77a, 77b and to generate a plurality of feed-back signals. First, a feed-back signals to the actuator 93 may be provided. The actuator 93 may relate to an actuator for controlling displacement of the first working element 74 and/or the second working element 75. The control unit 72c may further be arranged to provide a feed-back signal to a suitable user interface for indicating the force exerted by the first working element and/or the second working element. For example, the user interface may be part of the robotic unit 95, for example a regulator of a joy-stick 95a with which a displacement of the working elements may be initiated. As a result, the regulator may provide resistance force for displacement of the joy-stick 95a in response to the forces measured by the sensors 76a, . . . , 77b. In this way the operator is provided with an accurate feed-back regarding tissue resistance, for example. Alternatively, the user interface may comprise a computer program arranged to indicate relatively or absolutely the exerted forces. The computer program may also be arranged to control a resistance of the joy-stick 95a for providing accurate feed-back regarding tissue resistance to the operator. The computer program may be arranged to provide an upper limit to a possible force to be exerted by the first and/or the second working element for avoiding unnecessary tissue damage. Alternatively, the computer program may be arranged to provide a visual and/or auditive feed-back to the operator when the intended force to be exerted by the first and/or the second working element is to supersede an allowable limit.

Figure 10:
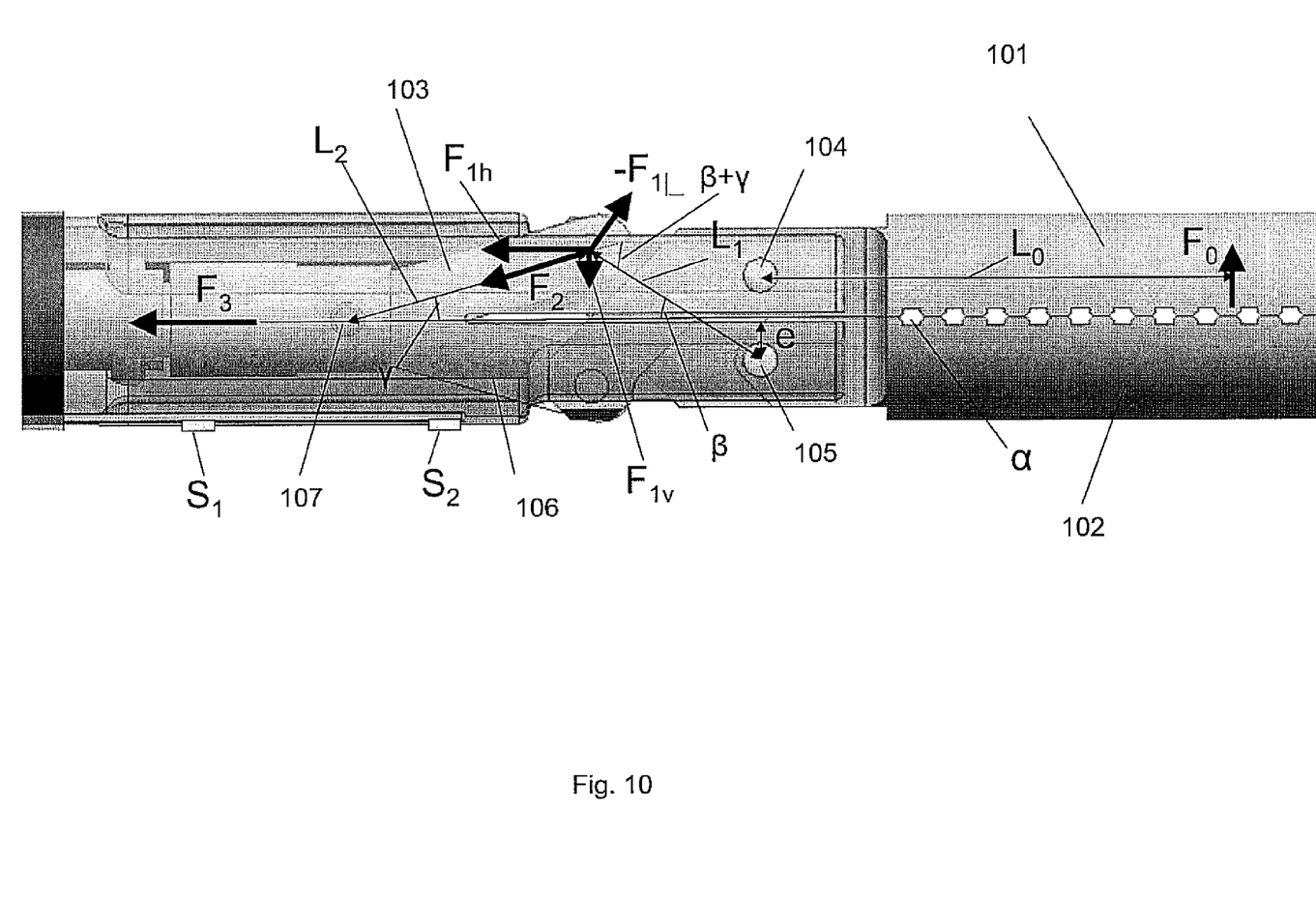
FIG. 10 presents a schematic view of a close-up of a distal portion of the device of FIG. 1 with forces and their mutual dependence indicated.

FIG. 10 shows schematically possible forces and their mutual dependencies in a forceps arrangement according to the current invention. For the sake of clarity just some mechanical parts of the forceps are provided with reference signs, however, it will be appreciated that forceps construction discussed with reference to any of FIG. 2-9 may be applicable here. The forceps comprises a first working element 101 cooperating with a hinge 104 and a second working element 102 cooperating with a second hinge 105. The hinges are operable using connecting bars 103, 106, which may have the same proximal fixation point 107.

Preferably, sensor $S_1$ only measures the actuation pulling force $F_3$ in the rod operating the first working element 101 and the second working element 102, whereas sensor $S_2$ measures a combination of gripping force $F_0$, actuation pulling force in the rod $F_3$, and vertical component of this rod force acting on the working elements.

The mutual dependencies between forces, lengths, and angles may be written as follows:

$$F_2 = \frac{F_3/2}{\cos(\gamma)}$$

$$F_1 = F_2 \sin(\beta + \gamma)$$

$$F_0 = F_1 \cdot L_1/L_0$$

$$L_2 \sin(\gamma) = L_1 \sin(\beta) - e$$

$$\beta = \beta_0 + \alpha$$

wherein
F0 is the gripping force acting on the working element.
F1 is the force exerted by the connecting bar on the leftmost point/hinge of the working element.
F2 is the force in the connecting bar.
F3 is the force in the pulling rod.
L1 is the left lever arm of the working element.
L2 is the length of the connecting bar.
α is forceps opening angle, i.e. the angle between the first working element and the second working element;
β is the angle between the horizontal and the left lever arm of the working element.
γ is the angle between the horizontal and the connecting bar.
e is the distance between the middle of the frame and the hinge of the working element.

The derived forces and angles may then be given by the following:

$$F_0 = \frac{F_3/2}{\cos(\gamma)} \frac{L_1}{L_0} \sin(\beta + \gamma)$$

$$F_{1h} = F_3/2$$

$$F_{1v} = F_{1h} \cdot \tan(\gamma)$$

$$\gamma = \arcsin\left(\frac{L_1 \sin(\beta) - e}{L_2}\right)$$

wherein the subscript "h" or "v" denotes a vertical or a horizontal component, respectively.

The sensor signals S1, S2 depending on the forces, lengths, and angles can be given by:

$$S_1 = F_3/2$$

$$S_2 = F_3/2 + f \cdot (F_0 + F_{1v})$$
$$= \frac{F_3}{2}\left\{1 + f \frac{L_1}{L_0} \frac{\sin(\beta + \gamma) + \sin(\gamma)}{\cos(\gamma)}\right\}$$
$$= F_0\left\{f + \frac{L_0}{L_1} \frac{\sin(\gamma) + \cos(\gamma)}{\sin(\beta + \gamma)}\right\}$$

Constant f gives the ratio between sensor sensitivity for vertical and horizontal forces on the hinges. Constant f might be derived by geometrical analysis, FEM analysis, or calibration of a real instrument.

From this derivation it is clear that the signal from sensor $S_2$ depends on the gripping force $F_0$, the position of tissue in the forceps $L_0$, and the opening angle of the forceps which is linked in a unique way to angle γ. Angle γ can be determined by simply measuring the displacement of the pulling rod, From the resulting equations force $F_0$ and length $L_0$ can be solved if both the sensors S1 and S2 are used.

In practice such an arrangement of sensors would be calibrated before use because both sensors might be sensitive to a combination of forces resulting in a sensitivity. Such sensitivity can be written in a matrix as follows:

$$\begin{bmatrix} S_1 \\ S_2 \end{bmatrix} = F_0 \cdot \begin{bmatrix} a & b \\ c & d \end{bmatrix} \begin{bmatrix} 1 \\ L_0 \end{bmatrix}$$

From which $F_0$ can be calculated:

$$F_0 = \frac{d \cdot S_1 - b \cdot S_2}{a \cdot d - b \cdot c}$$

Constants a, b, c, and d can be found by performing a measurement where gripping twice with the same force $F_0$ at two different positions in the forceps; at $L_{0,1}$ and $L_{0,2}$. This gives four sensor readings; two readings for sensor $S_1$: $S_{1,1}$ & $S_{1,2}$, and two readings for sensor $S_2$: $S_{2,1}$ & $S_{2,2}$. It then follows by common linear algebra that;

$$a = \frac{1}{F_0} \frac{L_{0,2} S_{1,1} - L_{0,1} S_{1,2}}{L_{0,1} - L_{1,2}}, \quad b = \frac{1}{F_0} \frac{S_{1,1} - S_{1,2}}{L_{0,1} - L_{0,2}}$$

$$c = \frac{1}{F_0} \frac{L_{0,2} S_{2,1} - L_{0,1} S_{2,2}}{L_{0,1} - L_{2,2}}, \quad d = \frac{1}{F_0} \frac{S_{2,1} - S_{2,2}}{L_{0,1} - L_{0,2}}$$

Using these constants an accurate determination of gripping force $F_0$ can be made, as long as the matrix with constants a, b, c, and d is sufficiently well conditioned. This can be accomplished by placing the sensors such that they are linearly independent.

Note that the above calibration is shown for a single opening angle only. For other angles an analytical model as given in FIG. 11 could be used, possibly complemented with additional calibrations at several opening angles.

Figure 11:
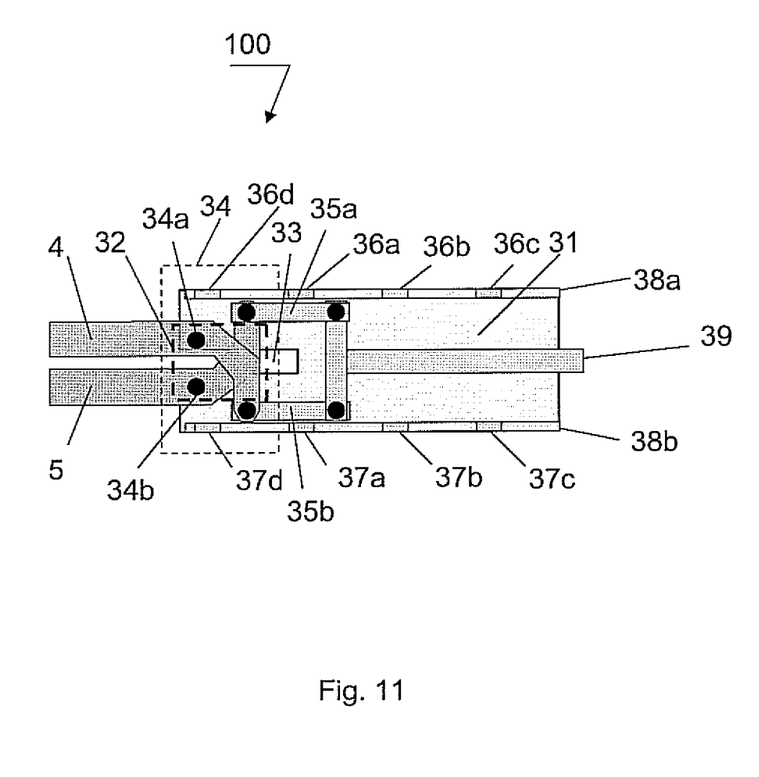
FIG. 11 presents schematic views of embodiments of the device with a decreased sensitivity for forces in the rod.

FIG. 11 presents a schematic view of an embodiment of the device with a decreased sensitivity for forces in the rod, which is based on the embodiment shown in FIG. 3. Accordingly, items discussed with reference to FIG. 3 are applicable here.

Embodiment 100 has decreased sensitivity for spurious forces because the connecting bars 35a and 35b are positioned horizontally. Angle γ in FIG. 10 is now small and consequently the effect of vertical force $F_1$, on sensor S2 is also small. Angle γ will become larger again if the working elements are opened.

It will be appreciated that although the slit between the origins of the first working element and the second working element is depicted to extend in a longitudinal direction, i.e. a direction along the frame 3, it is also possible to arrange the slit in a direction transverse to the direction of the frame. In this case the slit may divide the frame into two parts, each part connected with a working element. Each working element is arranged to transfer a corresponding force towards the part of the frame it cooperates with. In a particular embodiment the slit may be arranged perpendicular to a direction of frame 3 shown in FIG. 1. It will be further appreciated that the opening between the first working element and the second working element may be provided in any desirable form, for example, it may be a rectangular slit, or a circular or an oval shape.

In the embodiment 100 extra sensors may be provided. The extra sensors can be used to compensate for sensitivity to undesirable forces, such as the forces exerted by the connecting bars 35a, 35b between the working elements 4 and 5 and the rod 39. In such an arrangement sensors 36b/c and 37b/c are mainly measuring the effect of the pulling force in the rod, whereas sensors 36a and 37a are mainly measuring the force exerted by the jaws on the tissue plus an additional component of the rod force caused by the connecting bars 35a and 35b. This extra force depends on the rod force and the opening angle of the jaws. In the configuration of FIG. 3 the additional force is simply equal to half of the push or pull force in the rod times the tangent of the angle between the connecting bars and the rod. This force can therefore be compensated through the rod force measured with sensors 36b/37b and a sensor that measures the opening angle of the jaws, such as a sensor on the rod or an encoder on the motor driving the rod. Further details are given in FIG. 10.

Sensors 36d and 37d are largely insensitive to any forces but equally sensitive to temperature and can therefore be used to compensate for temperature effects.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below. It will further be appreciated that several mechanical layouts of the forceps are possible within the concept of the invention provided a slit or any other opening is arranged between the jaws of the forceps, said opening being arranged to guide the jaw reaction forces to separate parts of the frame of the surgical instrument.

The invention claimed is:

1. An instrument comprising:
   a frame, comprising:
      a proximal region;
      a distal region adjoining the proximal region, wherein the distal region is forked into a first prong and a second prong, each prong comprising a length from a point at which the respective prong meets the proximal region to a distal end of the respective prong, the prongs being separated from one another by a void that extends the entire length of the prongs, the prongs not being connected to one another anywhere along the lengths of the prongs;
   a first working element pivotably attached to the first prong at a first point;
   a second working element attached to the second prong at a second point, the second working element cooperating with the first working element to thereby exert a force between the first working element and the second working element;
   a first strain sensor disposed along the frame at or near the distal region and configured to measure a linear sum of a plurality of forces including at least a force exerted between the first and the second working elements and an actuation pulling force;
   a second strain sensor disposed along the frame further away from the distal region than the first strain sensor, the second strain sensor configured to measure an actuation pulling force along an axis of the frame; and
   a control unit configured to receive strain measurements from the first and second strain sensors and calculate the force exerted between the first and the second working elements by using the measurements from the second strain sensor as a reference for compensating for the actuation pulling force along the axis of the frame in the linear sum of a plurality of forces measured by the first strain sensor.

2. The instrument according to claim 1, wherein the void comprises a hole or a slit.

3. The instrument according to claim 1, wherein the first working element is pivotable about a hinge disposed at the first point.

4. The instrument according to claim 1, further comprising a strain sensor disposed on one of the working elements, the strain sensor being configured to measure a temperature of a region of the instrument near the distal end.

5. The instrument according to claim 1, wherein the control unit is further configured to determine a feedback signal.

6. The instrument according to claim 5, wherein the feedback signal is used to control the first working element.

7. The instrument according to claim 5, wherein the feedback signal is used to indicate the force exerted between the first working element and the second working element.

8. The instrument according to claim 6, further comprising a further actuator configured to control the first working element, wherein the feedback signal is provided to the further actuator.

9. The instrument according to claim 1, wherein at least one of the first strain sensor and the second strain sensor comprises at least one Fibre Bragg Grating (FBG) sensor.

10. The instrument according to claim 9, wherein at least one of the first strain sensor and the second strain sensor is a plurality of FBG sensors integrated on a mutual optical fiber.

11. The instrument according to claim 1, wherein a region of the frame comprising the distal end is removable from a remainder of the frame.

12. The instrument according to claim 1, further comprising an actuator disposed near the proximal end, wherein the actuator is configured to control movement of the first working element.

13. The instrument according to claim 1, wherein the second working element is pivotably attached to the frame at the second point.

14. The instrument according to claim 13, wherein the second working element is pivotable about a hinge disposed at the second point.

15. The instrument according to claim 1, wherein the first point lies across the void from the second point.

16. The instrument according to claim 1, further comprising a sensor to derive a measure ($\gamma$) for an opening angle between the first and second working elements.

17. The instrument according to claim 16, wherein the control unit is further configured to receive a measure for the opening angle and calculate a position ($L0$) where the force ($F0$) is exerted between the first and the second working elements based on the measure for the opening angle and the measurements from the first and second strain sensors.

18. The instrument according to claim 17, wherein the opening angle is derived by measuring displacement of a pulling rod actuating the first and/or second working elements.

19. The instrument according to claim 17, wherein the control unit is configured to calculate the force exerted between the first and the second working elements using calibration data of a relative sensitivity of the first and second sensors to the force.

* * * * *